United States Patent
Jung et al.

(10) Patent No.: US 6,312,865 B1
(45) Date of Patent: Nov. 6, 2001

(54) SEMICONDUCTOR DEVICE USING POLYMER-CONTAINING PHOTORESIST, AND PROCESS FOR MANUFACTURING THE SAME

(75) Inventors: Min Ho Jung; Jae Chang Jung; Cheol Kyu Bok; Ki Ho Baik, all of Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 09/223,510

(22) Filed: Dec. 30, 1998

(30) Foreign Application Priority Data

Dec. 31, 1997 (KR) .................................................. 97-81403

(51) Int. Cl.$^7$ ................................. G03F 7/39; G03F 7/30
(52) U.S. Cl. ........................ 430/270.1; 430/18; 430/320; 430/326; 526/75; 526/325
(58) Field of Search ................................... 430/270.1, 18, 430/320, 326; 526/75, 325

(56) References Cited

U.S. PATENT DOCUMENTS

| | | | |
|---|---|---|---|
| 3,715,330 | * 2/1973 | Nogami et al. | 260/40 |
| 4,106,943 | 8/1978 | Ikeda et al. | 96/192 |
| 4,202,955 | 5/1980 | Gaylord | 526/272 |
| 4,491,628 | 1/1985 | Ito et al. | 430/176 |
| 4,883,740 | 11/1989 | Schwaim et al. | 430/270 |
| 5,212,043 | 5/1993 | Yamamoto et al. . | |
| 5,252,427 | 10/1993 | Bauer et al. | 430/270 |
| 5,843,624 | 12/1998 | Houlihan et al. | 430/296 |
| 5,849,808 | 12/1998 | Schacht et al. | 522/31 |
| 6,028,153 | * 2/2000 | Jung | 526/258 |
| 6,048,664 | * 4/2000 | Houlihan et al. | 430/270.1 |
| 6,063,542 | * 5/2000 | Hyeon et al. | 430/270.1 |
| 6,132,926 | * 10/2000 | Jung et al. | 430/270.1 |
| 6,136,499 | * 10/2000 | Goodall et al. | 430/270.1 |
| 6,143,466 | * 11/2000 | Choi | 430/270.1 |

FOREIGN PATENT DOCUMENTS

| | | | |
|---|---|---|---|
| 0071571 | 7/1982 | (EP) | G03C/1/68 |
| 0 291 970 | 5/1988 | (EP) . | |
| 794458 | 9/1997 | (EP) . | |
| 0836119A1 | 11/1997 | (EP) . | |
| 1342112 | 5/1970 | (GB) | C07C/69/74 |
| 1342112 | 12/1973 | (GB) . | |
| 2320717 | 6/1997 | (GB) | C08F/232/04 |
| 1484061 | 8/1997 | (GB) | C08J/3/28 |
| 2320718 | 12/1997 | (GB) | C08F/32/08 |
| 2321060 | 1/1998 | (GB) | C08F/232/08 |
| 2332679A | 6/1999 | (GB) | C08F/232/08 |
| 11286469 | * 10/1999 | (JP) . | |
| 1010914 | 8/1999 | (NL) . | |
| WO 96/37526 | 11/1996 | (WO) . | |
| WO 97/33198 | 9/1997 | (WO) . | |

OTHER PUBLICATIONS

U.S. application No. 09/222,053, filed Dec. 29, 1998, Jung et al.

James V. Crivello and Sang-Yeon Shim, Chemically Amplified Electron-Beam Photoresists, *Chemical Mater.*, (1966) vol. 8, pp. 376-381.

S. J. Choi et al., New ArF Single Layer Resists for 193-nm Lithography, 1997, *Journal of Photopolymer Science and Technology*, vol. 10, 521-528.

Alexander A. Dobrev, Emile Perez, Jean Claud Ader, Armand Lattes, First Application of Functionalized in the Ester Moiety Acrylates in Diels-Alder Reaction: Influence of Solvents on Stereochemistry, *Bulgarian Chemical Commjnications*, vol. 28, No. 2 (1995) pp. 253-258.

Uzodinma Okoroanyanwu et al., New Single Layer Positive Photoresists for 193 nm Photolithography, *SPIE*, vol. 3049, 1997, pp. 92-103.

CA 130:229879.

Registry No. 37503-43-8.

Thomas I. Wallow, et al., "Evaluation of Cycloolefin-Maleic Anhydride Alternating Copolymers as Single-Layer Photoresist for 193nm Photolithography," *Proc. SPIE*, vol. 2724, 1996, pp. 355-364.

R.D. Allen et al., "The Influence of Photoacid Structure on the Design and Performance of 193nm Resists," *Journal of Photopolymer Science and Technology*, vol. 10, 1997, pp. 503-510.

F.M. Houlihan et al., "A Commercially Viable 193nm single Layer Resist Platform", *Journal of Photopolymer Science and Technology*, vol. 10, 1997, pp. 511-520.

T. Hattori et al., "Synthesis an Dissolution Characteristics of Novel Alicycli Polymer With Monoacid Ester Structures," *Journal of Photopolymer Science and Technology*, vol. 10, 1997, pp. 533-544.

(List continued on next page.)

*Primary Examiner*—Janet Baxter
*Assistant Examiner*—Yvette M. Clarke
(74) *Attorney, Agent, or Firm*—Townsend and Townsend and Crew LLP

(57) ABSTRACT

The present invention relates to a semiconductor device using a copolymer-containing photoresist, and a process for manufacturing the same. As a norbornene derivative (monomer) having a hydrophilic group is synthesized and introduced to the backbone chain of a polymer, the polymer according to the present invention has excellent etching resistance and heat resistance, which are the characteristic points of alicyclic olefin structure, and provide excellent resolution due to prominent enhancement of adhesiveness resulted from introducing a hydrophilic group (—OH).

12 Claims, 1 Drawing Sheet

OTHER PUBLICATIONS

K. Nozaki and Ei Yaro, "New Protective Groups in Methacrylate Polymer for 193–nm Resists," *Journal of Photopolymer Science and Technology,* vol. 10, 1997, pp. 545–550.

ArF Single Layer Resist Composed of Alicyclic Main Chain Containing Maleic Anhydride, Jae Chang Jung, Cheol Kyu Bok and Ki Ho Baik; Jouranl of Photopolymer Science and Technology, vol. 10, No. 4 (1997) pp. 529–534.

First Application of Funtionalized in the Ester Moiety Acrylates in Diels–Alder Reaction: Influence of Solvents on Stereochemistry; Alexander A. Dobrev, Emile Perez, jean Claud Ader, Armand Lattes; Bulgarian Chemical Communications, vol. 28, No.2, (1995) pp. 253–258.

Mosquito Repellants: Monocarboxylic Esters of Aliphatic Diols; T.P. McGovern and C.E. Schreck; Journal of the American Mosqito Control Association, vol. 4, No. 3, pp. 314–321–.

S. J. Choi et al., "New ArF Single–layer Resist for 193–nm Lithography", 1997, Journal of Photopolymer Science and Technology, vol. 10, 521–528.

K. Nakano et al., "Chemically Amplified Resist Based on High Etch–Resistant Polymer for 193–nm Lithography", 1997, Journal of Photopolymer Science and Technology, vol. 10, 561–569.

CA Register No. 194997–59–6.

CA Abstract No. 127:227269 & J Photopolym. Sci. Technol. 10(4) 529–534 (1997).

* cited by examiner

SEMICONDUCTOR DEVICE USING POLYMER-CONTAINING PHOTORESIST, AND PROCESS FOR MANUFACTURING THE SAME

BACKGROUND OF THE INVENTION

The present invention relates to semiconductor devices using a photoresist, and to processes for manufacturing the same.

Various types of photoresists have been used or proposed. These resists should have a variety of desirable characteristics or properties. In general, all or most of these resists generally demand etching resistance, adhesiveness with low light absorption at 193 nm wavelength for ArF. Additionally, the resists should be developable by using 2.38 wt % aqueous tetramethylammonium hydroxide (TMAH) solution. It is, however, difficult to synthesize a polymer satisfying one or all these properties.

Many researches have focused on studies on norbolac type resin as a resin to increase transparency at 193 nm wavelength and increase etching resistance. As merely an example, "Bell Labs" tried to introduce alicyclic unit to the backbone chain of a copolymer in order to enhance etching resistance. A copolymer resin in which the backbone chain has norbornene, acrylate and maleic anhydride substituent, as represented by chemical formula I has been suggested:
[FORMULA I] See Appendix A In the polymer resin of formula I, the maleic anhydride portion (portion A) was used for polymerizing alicyclic olefin group.

The maleic anhydride portion is soluble in 2.38% aqueous TMAH solution even it is not exposed, and thus a y-portion having tert-butyl substituent should be highly increased in order to prevent dissolution. But increase of the y-portion causes relative decrease of z portion, which enhances sensitivity and adhesiveness with substrate, to cause disadvantage in that photoresist is removed from the wafer in practical patterning.

Thus, an effective pattern cannot be formed without separately using a solubility controlling agent, and even if a pattern is formed by using a solubility controlling agent, the adhesiveness is too poor to be applied to practical patterning.

Under such circumstances, Bell Labs tried to solve the above-mentioned problems by using a solubility controlling agent of cholesterol type and by employing two-component resist comprising a polymer of cyclo-olefin and maleic anhydride.

However, in this case, very large amount (about 30% by weight based on the polymer) of the solubility controlling agent should be used, and thus the polymer of the above molecular structure basically has too low reproducibility and too high cost to be used as a polymer for a photoresist. From the above, it is seen that an improved photoresist resin that is cost effective, easy to manufacture, and has desirable other properties is clearly desired.

SUMMARY OF THE INVENTION

The present inventors have performed intensive studies to overcome the above limitations encountered in conventional resins, and as a result, they could synthesize novel norbornene derivatives having hydrophilic group(s). In a specific embodiment, the present invention provides a method using a step of introducing the monomer to the backbone chain of the polymer to develop a polymer having excellent resolution due to prominent enhancement of adhesive strength by introducing a hydrophilic group (—OH). The present method yields a photoresist having excellent etching resistance and heat resistance which are the characteristics of alicyclic olefins.

Numerous benefits or advantages are achieved by way of the present invention over conventional techniques. In a specific embodiment, the present invention provides a monomer comprising a novel norbornene derivative represented by following formula II:
[FORMULA II] See Appendix A
wherein, R' and R" independently represent hydrogen, or linear or branched $C_1$–$C_4$ alkyl group with or without substituent(s), m represents number of 1 to 8, and n represents number of 1 to 6, and a process for preparing the same.

In an alternative embodiment, the present invention provides a polymer for a photoresist comprising bicycloalkene compounds represented by chemical formulas II and V, and maleic anhydride of chemical formula VI, and a process for preparing the same.

In a further embodiment, the present invention provides a polymer for photoresist represented by formula III or IV, which comprises bicycloalkene compound(s) and maleic anhydride, and process for preparing the same.
[FORMULA III] See Appendix A
[FORMULA IV] See Appendix A
In the formula, R' and R" independently represent hydrogen, or linear or branched $C_1$–$C_4$ alkyl group with or without substituent (s), $R_1$ and $R_2$ independently represent hydrogen, or linear or branched alkyl, cycloalkyl, alkoxyalkyl or cycloalkoxyalkyl having 1 to 10 carbon atoms with or without substituent(s), m represents number of 1 to 8, and the ratio x: y: z is (0–99%) : (0–99%) : (0–99%) [provided that x is 0.005–0.9 part by mole, and y and z are 0.001–0.9 part by mole, respectively, in case of formula IV].

In still a further embodiment, the present invention provides a polymer for photoresist which comprises bicycloalkene compounds represented by formulas II and V, and maleic anhydride represented by formula VI, and a photoresist formed by using a polymer represented by formula III, IV, VII, VIII or IX, and a process for manufacturing the photoresist.
[FORMULA V] See Appendix A
[FORMULA VI] See Appendix A Still further, the present invention provides a polymer for photoresist. The polymer includes a variety of elements such as bicycloalkene compounds represented by formulas II and V, and maleic anhydride represented by formula VI, and a process for forming a photoresist pattern by the use of the photoresist formed with the polymer represented by formula III, IV, VII, VIII or IX.

Moreover, the present invention provides a polymer for photoresist. The present polymer includes a variety of elements such as bicycloalkene compounds represented by formulas II and V, and maleic anhydride represented by formula VI, and a semiconductor device using the photoresist formed with the polymer represented by formula III, IV, VII, VIII or IX.
[FORMULA VII] See Appendix A
[FORMULA VIII] See Appendix A
[FORMULA IX] See Appendix A

DETAILED DESCRIPTION OF THE INVENTION

Figure 1:
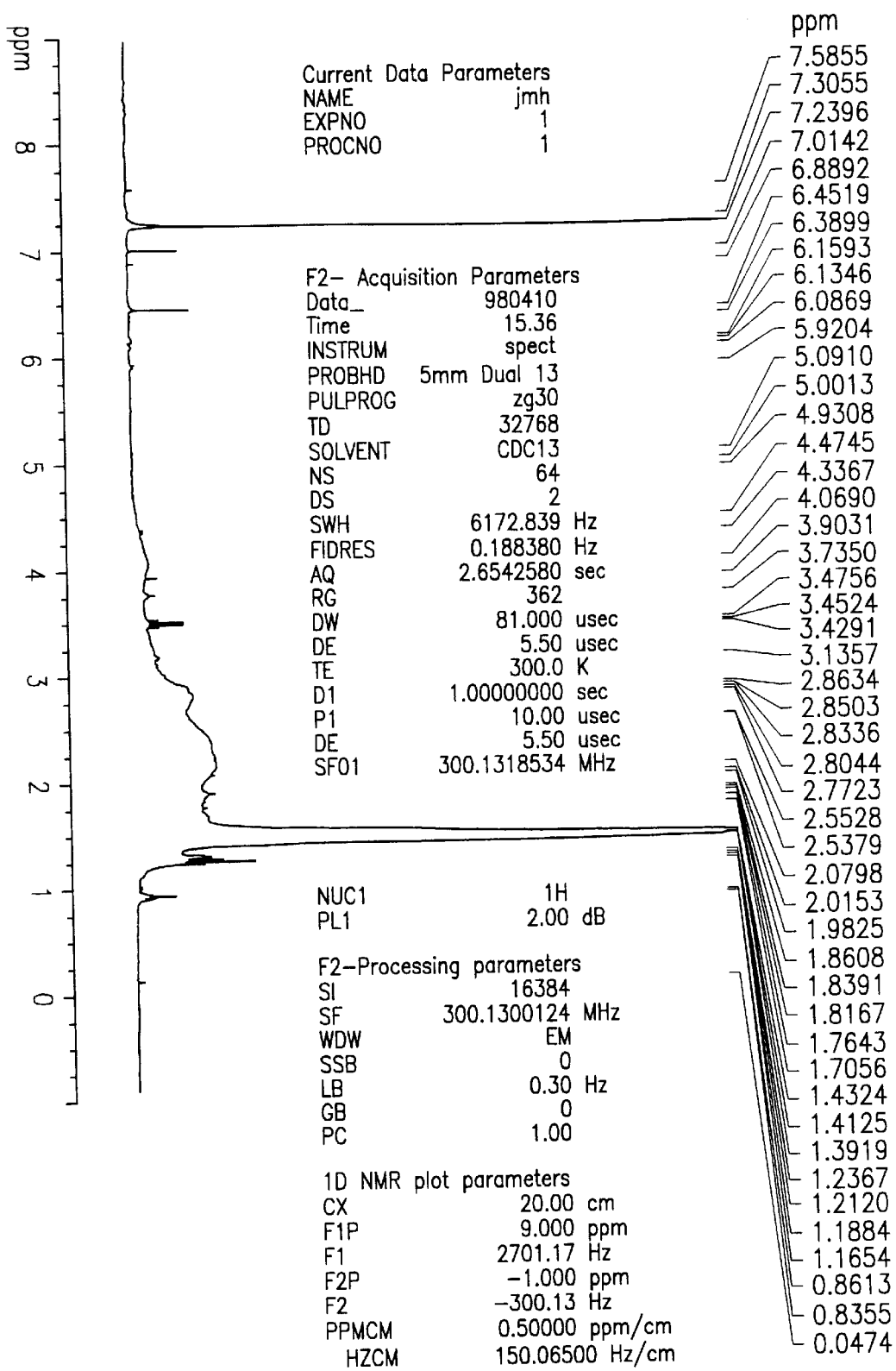
FIG. 1 illustrates NMR data of the polymer prepared in Example 9.

The present invention is embodied in a polymer usable for lithography process using ultra-short wavelength light source such as KrF (248 nm), ArF (193 nm), X-ray, ion beam and E-beam which is expected to be applied in 1G or 4G DRAM or other highly integrated circuits, and having a novel norbornene monomer introduced to the backbone chain of the polymer. The invention is further embodied in a process for manufacturing the same, and a photoresist containing the same polymer.

Among the bicycloalkene compounds represented by formula II, preferable compounds are 3-hydroxypropyl 5-norbornen-2-carboxylate, 4-hydroxybutyl 5-norbornen-2-carboxylate, 5-hydroxypentyl 5-norbornen-2-carboxylate, 6-hydroxyhexyl 5-norbornen-2-carboxylate, 7-hydroxyheptyl 5-norbornen-2-carboxylate, 8-hydroxyoctyl 5-norbornen-2-carboxylate, or the like.

The bicycloalkene derivatives (formula II) according to the present invention can be prepared by reacting hydroxyalkyl acrylate with cyclopentadiene in the presence of tetrahydrofuran.

The hydroxyalkyl acrylate is preferably selected from a group consisting of 3-hydroxypropyl acrylate, 4-hydroxybutyl acrylate, 5-hydroxypentyl acrylate, 6-hydroxyhexyl acrylate, 7-hydroxyheptyl acrylate and 8-hydroxyoctyl acrylate.

The polymer according to the present invention (formula III or IV) can be prepared by polymerizing the bicycloalkene compounds represented by chemical formulas II and V and maleic anhydride represented by formula VI in the presence of polymerization initiator.

Preferable bicycloalkenes to be used for the polymers for photoresist according to the present invention may be one or more compounds selected from a group consisting of bicycloalkenes represented by formula V wherein R is hydrogen or tert-butyl group, and bicycloalkenes represented by formula II wherein m is 3 and R' and R" are hydrogen.

More preferably, bicycloalkenes for the polymers according to the present invention are selected from a group consisting of 3-hydroxypropyl 5-norbornen-2-carboxylate, tert-butyl 5-norbornen-2-carboxylate, 5-norbornen-2-carboxylic acid, 3-hydroxypropyl bicyclo[2,2,2]oct-5-en-3-carboxylate, tert-butyl bicyclo[2,2,2-oct-2-en-carboxylate and bicyclo[2,2,2]oct-5-en-2-carboxylic acid.

Among the polymers according to the present invention, the polymers prepared from the bicycloalkene represented by formula V wherein R is hydrogen or tert-butyl and n is 1, the bicycloalkene represented by formula II wherein R' and R" are hydrogen and m is 3 [i.e., one or more bicycloalkenes selected from a group consisting of 3-hydroxypropyl 5-norbornen-2-carboxylate, tert-butyl 5-norbornen-2-carboxylate and 5-norbornen-2-carboxylic acid], and maleic anhydride represented by formula VI are particularly preferable.

The polymers according to the present invention can be prepared by a conventional polymerization process such as bulk polymerization or solution polymerization. Polymerization initiators usable in the present invention include benzoyl peroxide, 2,2'-azobisisobutyronitrile (AIBN), acetyl peroxide, lauryl peroxide, tert-butyl peracetate, di-tert-butyl peroxide, or the like.

As a solvent, cyclohexanone, methyl ethyl ketone, benzene, toluene, dioxane, dimethylformamide and/or tetrahydrofuran may be used individually, or in a mixture.

In the process for preparing the polymers according to the present invention, general polymerization condition including temperature and pressure of radical polymerization may be controlled dependent upon the property of the reactants, but it is preferable to carry out the polymerization reaction at a temperature between 60 and 200° C. for 4 to 24 hours.

The polymers represented by formula III or IV according to the present invention have molecular weight of 3,000–100,000, and can be used in lithography process using ultra-short wavelength light such as KrF or ArF light source, X-ray, ion beam or E beam, which is expected to be applied to 1G or 4G DRAM.

The polymers according to the present invention may be used in the formation of a positive micro-image by preparing a photoresist solution in which the polymer is mixed with an organic solvent and a conventional photo acid generator according to a conventional process for preparing a photoresist composition.

In the process for forming photoresist pattern of semiconductor element, the amount of the polymer according to the present invention depends on the organic solvent or photo acid generator used, and the condition of lithography, but conventionally it is about 10 to 30% by weight on the basis of the organic solvent used in the preparation of the photoresist.

The process for forming a photoresist pattern of a semiconductor element by using the polymer according to the present invention is described in detail here-in-below:

The polymer according to the present invention is dissolved in cyclohexanone, methyl 3-methoxypropionate, ethyl 3-ethoxypropionate, ethyl lactate or propylene glycol methyl ether acetate at a concentration of 10 to 30% by weight. Onium salt or organic sulfonic acid as inorganic acid generator (0.01–10% by weight based on the polymer) is incorporated to the solution, and the mixture is then filtered through an ultra-micro filter to prepare photoresist solution.

As the photo acid generator, triphenylsulfonium triplate, dibutylnaphthylsulfonium triplate, 2,6-dimethylphenylsulfonate, bis(arylsulfonyl)-diazomethane, oxime sulfonate and 1,2-diazonaphthoquinon-4-sulfonate can be mentioned.

Then, the photoresist solution is spin-coated on a silicon wafer to form a thin film, which is then pre-baked in an oven at 80–150° C. or on a hot plate for 1–5 minutes, exposed to light by using far ultraviolet exposer or an eximer laser exposer, and post-baked in an oven at a temperature between 100° C. and 200° C. or on a hot plate for 1 second to 5 minutes.

The exposed wafer is impregnated in 2.38% aqueous TMAH solution for 30 seconds to 1.5 minutes to obtain an ultra-micro positive photoresist pattern.

The syntheses of novel norbornene derivatives according to the present invention, the syntheses of polymers using the derivatives, manufacturing the photoresist comprising the polymers, and process for forming micro-patterns in a semiconductor device are described in detail by referring to Examples.

A better understanding of the present invention may be obtained in light of following examples which are set forth to illustrate, but are not to be construed to limit, the present invention.

Syntheses of Norbornen Derivatives

EXAMPLE I

Synthesis of 3-hydroxypropyl 5-norbornene-2-carboxylate

In a reactor, cyclopentadiene (66 g) and tetrahydrofuran solvent (500 g) were charged, and the mixture was stirred homogeneously. To the reaction mixture, 3-hydroxypropyl acrylate (130 g) was added, and the resultant mixture was stirred at a temperature between −30° C. and 60° C. for about 10 hours to carry out the reaction.

When the reaction was completed, the solvent was removed by using a rotary evaporator, and the residue was distilled under reduced pressure to obtain 168 g (yield: 86%) of 3-hydroxypropyl 5-norbornene-2-carboxylate.

EXAMPLE II
Synthesis of 4-hydroxybutyl 5-norbornen-2-carboxylate

The same procedure described in Example I was repeated but 4-hydroxybutyl acrylate (144 g) was used instead of 3-hydroxypropyl acrylate to give 178 g (yield: 85%) of 4-hydroxybutyl 5-norbornen-2-carboxylate.

EXAMPLE III
Synthesis of 5-hydroxypentyl 5-norbornen-2-carboxylate

The same procedure described in Example I was repeated but 5-hydroxypentyl acrylate (158 g) was used instead of 3-hydroxypropyl acrylate to give 190 g (yield: 85%) of 5-hydroxypentyl 5-norbornen-2-carboxylate.

EXAMPLE IV
Synthesis of 6-hydroxyhexyl 5-norbornen-2-carboxylate

The same procedure described in Example I was repeated but 6-hydroxyhexyl acrylate (172 g) was used instead of 3-hydroxypropyl acrylate to give 205 g (yield: 86%) of 6-hydroxyhexyl 5-norbornen-2-carboxylate.

EXAMPLE V
Synthesis of 7-hydroxyheptyl 5-norbornen-2-carboxylate

The same procedure described in Example I was repeated but 7-hydroxyheptyl acrylate (186 g) was used instead of 3-hydroxypropyl acrylate to give 204 g (yield: 81%) of 7-hydroxyheptyl 5-norbornen-2-carboxylate.

EXAMPLE VI
Synthesis of 8-hydroxyoctyl 5-norbornen-2-carboxylate

The same procedure described in Example I was repeated but 8-hydroxyoctyl acrylate (200 g) was used instead of 3-hydroxypropyl acrylate to give 207 g (yield: 78%) of 8-hydroxyoctyl 5-norbornen-2-carboxylate.

Synthese of Bicycloalkene Compounds

EXAMPLE VII
Synthesis of tert-butyl 5-norbornen-2-carboxylate

In a reactor, cyclopentadiene (66 g) and tetrahydrofuran solvent (500 g) were charged, and the mixture was stirred homogeneously. To the reaction mixture, tert-butyl acrylate (128 g) was added, and the resultant mixture was stirred at a temperature between −30° C. and 60° C. for about 10 hours to carry out the reaction.

When the reaction was completed, the solvent was removed by using a rotary evaporator, and the residue was distilled under reduced pressure to obtain 175 g (yield: 90%) of tert-butyl 5-norbornene-2-carboxylate.

EXAMPLE VIII
Synthesis of 5-norbornen-2-carboxylic acid

In a reactor, cyclopentadiene (66 g) and tetrahydrofuran solvent (500 g) were charged, and the mixture was stirred homogeneously.

To the reaction mixture, acrylic acid (72 g) was added, and the resultant mixture was stirred at a temperature between—30° C. and 60° C. for about 10 hours to carry out the reaction.

When the reaction was completed, the solvent was removed by using a rotary evaporator, and the residue was distilled under reduced pressure to obtain 124 g (yield: 90%) of 5-norbornen-2-carboxylic acid.

Syntheses of Polymers

EXAMPLE IX
Synthesis of poly[3-hydroxypropyl 5-norbornen-2-carboxylate tert-butyl 5-norbornen-2-carboxylate/5-norbornen-2-carboxylic acid/maleic anhydride] polymer (Formula VII)

In tetrahydrofuran, benzene or toluene, dissolved were 3-hydroxypropyl 5-norbornen-2-carboxylate (0.05–0.8 mol), tert-butyl 5-norbornen-2-carboxylate (0.5–0.95 mol), 5-norbornen-2-carboxylic acid (0.01–0.3 mol) and maleic anhydride (1 mol).

Then, 2,2'-azobisisobutyronitrile (AIBN) (0.01–10 g), as a polymerization initiator, was added thereto, and the reaction was performed at a temperature between 60° C. and 70° C. for 4–24 hours.

Crude product thus obtained was precipitated from ethyl ether or hexane, and the precipitate was filtered and dried under reduced pressure to give poly[3-hydroxypropyl 5-norbornen-2-carboxylate/tert-butyl 5-norbornen-2-carboxylate/5-norbornen-2-carboxylic acid/maleic anhydride] polymer represented by formula VII, of which the NMR data is shown in FIG. 1. (yield: ≧70%)

EXAMPLE X
Synthesis of poly[4-hydroxybutyl 5-norbornen-2-carboxylate/tert-butyl 5-norbornen-2-carboxylate/5-norbornen-2-carboxylic acid/maleic anhydride] polymer (Formula VIII)

In tetrahydrofuran, benzene or toluene, dissolved were 4-hydroxybutyl 5-norbornen-2-carboxylate (0.05–0.8 mol), tert-butyl 5-norbornen-2-carboxylate (0.5–0.95 mol), 5-norbornen-2-carboxylic acid (0.01–0.3 mol) and maleic anhydride (1 mol).

Then, 2,2'-azobisisobutyronitrile (AIBN) (0.01–10 g), as a polymerization initiator, was added thereto, and the reaction was performed at a temperature between 60° C. and 70° C. for 4–24 hours.

Crude product thus obtained was precipitated from ethyl ether or hexane, and the precipitate was filtered and dried under reduced pressure to give poly[4-hydroxybutyl 5-norbornen-2-carboxylate/tert-butyl 5-norbornen-2-carboxylate/5-norbornen-2-carboxylic acid/maleic anhydride] polymer represented by formula VIII (yield:≧70%).

EXAMPLE XI
Synthesis of poly[3-hydroxypropyl 5-norbornen-2-carboxylate/tert-butyl 5-norbornen-2-carboxylate/mono-methyl cis-5-norbornen-endo-2,3-dicarboxylate/maleic anhydride] polymer (Formula IX)

In tetrahydrofuran, benzene or toluene, dissolved were 3-hydroxypropyl 5-norbornen-2-carboxylate (0.05–0.8 mol), tert-butyl 5-norbornen-2-carboxylate (0.5–0.95 mol), mono-methyl cis-5-norbornen-endo-2,3-dicarboxylate (0.01–0.3 mol) and maleic anhydride (1 mol).

Then, 2,2'-azobisisobutyronitrile (AIBN) (0.01–10 g), as a polymerization initiator, was added thereto, and the reaction was performed at a temperature between 60° C. and 70° C. for 4–24 hours.

Crude product thus obtained was precipitated from ethyl ether or hexane, and the precipitate was filtered and dried under reduced pressure to give poly[3-hydroxypropyl 5-norbornen-2-carboxylate/tert-butyl 5-norbornen-2-carboxylate/mono-methyl cis-5-norbornen-endo-2,3- dicarboxylate/maleic anhydride] polymer represented by formula IX (yield: 74%).

Preparation of Photoresist and Pattern Formation

EXAMPLE XII

Poly[3-hydroxypropyl 5-norbornen-2-carboxylate/tert-butyl 5-norbornen-2-carboxylate/5-norbornen-2-carboxylic acid/maleic anhydride] polymer (formula VII) (10 g) was dissolved in 3-methoxymethyl propionate (40 g, solvent), and triphenylsulfonium triplate or dibutylnaphthylsulfonium triplate (about 0.01–1 g) as a photo acid generator, was added thereto. After stirring, the mixture was filtered through a 0.1 μm filter to give a photoresist. Then the photoresist was coated on a surface of a wafer. After heat treatment, the photoresist was developed by a photo-developing process to form a pattern. Thus, a semiconductor element having perpendicular L/S pattern with thickness of the polymer 0.6 μm and the width of 0.13 μm was obtained.

EXAMPLE XIII

Poly[3-hydroxypropyl 5-norbornen-2-carboxylate/tert-butyl 5-norbornen-2-carboxylate/mono-methyl cis-5-norbornen-2-endo-2,3-dicarboxylate/maleic anhydride] polymer (formula IX) (10 g) was dissolved in 3-methoxymethyl propionate (40 g, solvent), and triphenylsulfonium triplate or dibutylnaphthylsulfonium triplate (about 0.01–1 g) as a photo acid generator, was added thereto. After stirring, the mixture was filtered through a 0.1 μm filter to give a photoresist. Then the photoresist was coated on a surface of a wafer. After heat treatment, the photoresist was developed by a photo-developing process to form a pattern. Thus, a semiconductor element having perpendicular L/S pattern with thickness of the polymer 0.6 μm and the width of 0.13 μm was obtained.

As described above, the photoresist formed by using the polymers for KrF or ArF according to the present invention has excellent etching resistance, heat resistance and adhesiveness, and is developable with 2.38% aqueous TMAH solution, so that satisfactory results can be obtained in view of resolution of perpendicular L/S pattern of 0.13 μm with resist thickness of 0.6 μm, and the depth of a focus.

Many modifications and variations of the present invention are possible in light of the above teachings. Therefore, it is to be understood that within the scope of the appended claims, the invention may be practiced otherwise than as specifically described.

APPENDIX A

FORMULA I

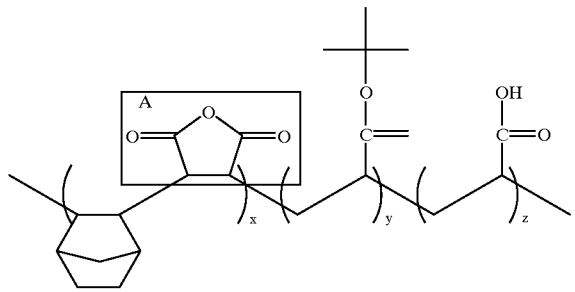

FORMULA II

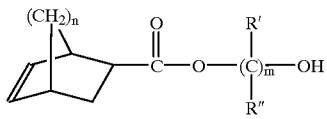

FORMULA III

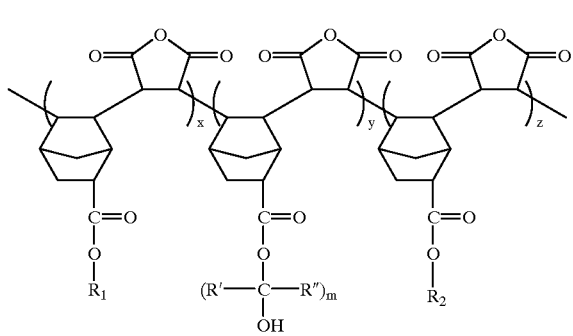

FORMULA IV

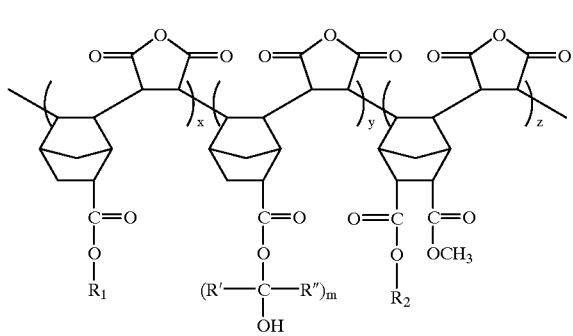

FORMULA V

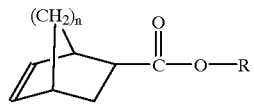

FORMULA VI

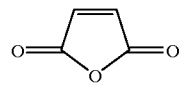

FORMULA VII

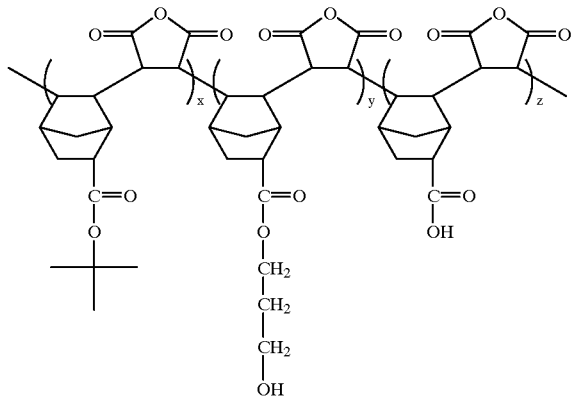

-continued

FORMULA VIII

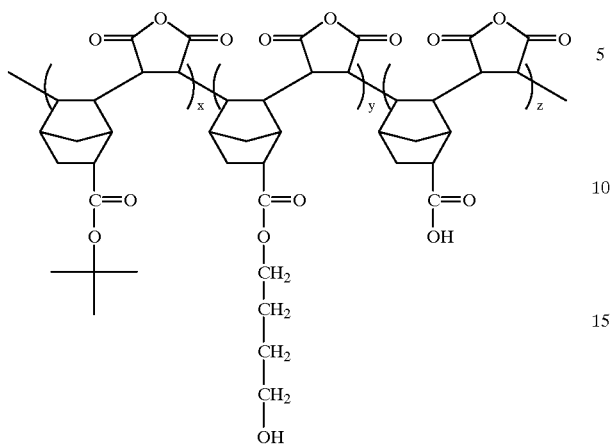

FORMULA IX

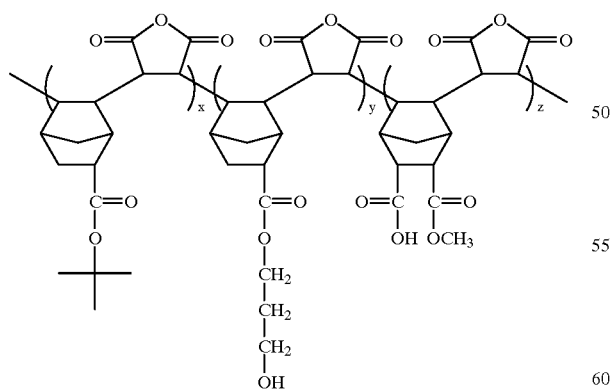

What is claimed is:

1. A polymer comprising poly[3-hydroxypropyl 5-norbornene-2-carboxylate/tert-butyl 5-norbornene-2-carboxylate/mono-methyl cis-5-norbornene-endo-2,3-dicarboxylate/maleic anhydride] represented by formula IX:

FORMULA IX

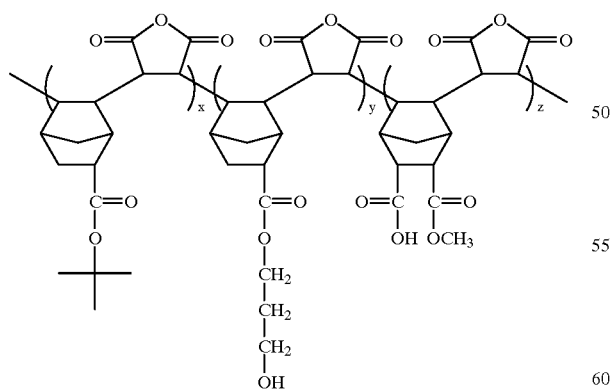

wherein the molar ratio x:y:z is (0.1%–99%):(0.1%–99%):(0.1%–99%).

2. A polymer comprising a photoresist polymer represented by formula IV:

FORMULA IV

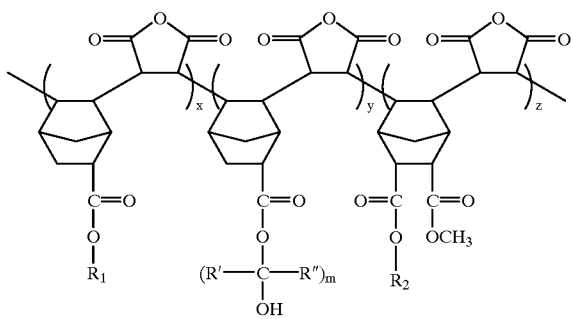

wherein

R' and R" independently represent hydrogen, or a linear or branched $C_1$–$C_4$ alkyl group with or without substituent(s);

$R_1$ and $R_2$ independently represent hydrogen, or linear or branched alkyl, cycloalkyl, alkoxyalkyl or cycloalkoxyalkyl having 1 to 10 carbon atoms with or without substituent(s);

m represents a number of 1 to 8; and the molar ratio x:y:z is (0.005–0.9):(0.001–0.9):(0.001–0.9).

3. A photoresist composition comprising:

(a) a photoresist polymer, (b) a solvent, and (c) a photoacid generator;

wherein said photoresist polymer is poly[3-hydroxypropyl 5-norbornene-2-carboxylate/tert-butyl 5-norbornene-2-carboxylate/mono-methyl cis-5-norbornene-endo-2,3-dicarboxylate/maleic anhydride] or a polymer of formula IV:

FORMULA IV

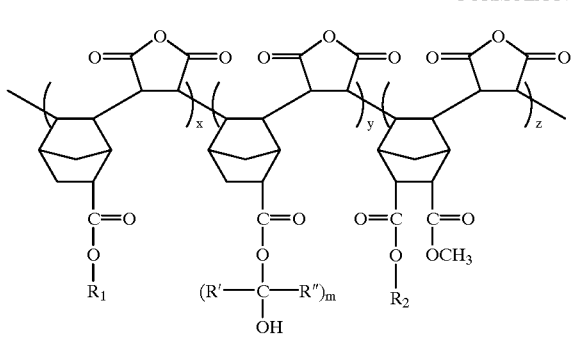

wherein

R' and R" independently represent hydrogen, or a linear or branched $C_1$–$C_4$ alkyl group with or without substituent(s);

R₁ and R₂ independently represent hydrogen, or linear or branched alkyl, cycloalkyl, alkoxyalkyl or cycloalkoxyalkyl having 1 to 10 carbon atoms with or without substituent(s);

m represents a number of 1 to 8; and the molar ratio $x:y:z$ is $(0.005–0.9):(0.001–0.9):(0.001–0.9)$.

4. The photoresist composition of claim 3, wherein the amount of said photoresist polymer present in said composition is between 10 and 30% by weight based on the amount of said solvent.

5. The photoresist composition of claim 3, wherein said solvent is selected from the group consisting of cyclohexanone, methyl 3-methoxypropionate, ethyl 3-ethoxypropionate, ethyl lactate, propylene glycol methyl ether acetate, and mixtures thereof.

6. The photoresist composition of claim 3, wherein said photoacid generator is an onium salt or an organic sulfonic acid.

7. The photoresist composition of claim 3, wherein the amount of said photoacid generator present in said composition is between 0.01 and 10% by weight based on the amount of said photoresist polymer.

8. A process for producing a photoresist composition, said process comprising the steps of:

(a) adding a photoresist polymer and a photoacid generator to a solvent to form a photoresist solution; and (b) filtering said photoresist solution to form said photoresist composition, wherein said photoresist polymer is poly[3-hydroxypropyl 5-norbornene-2-carboxylate/tert-butyl 5-norbornene-2-carboxylate/mono-methyl cis-5-norbornene-endo-2,3-dicarboxylate/maleic anhydride] or a polymer of formula IV:

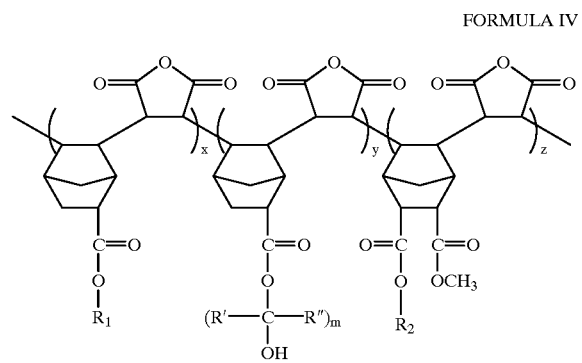

FORMULA IV

R' and R" independently represent hydrogen, or a linear or branched $C_1$–$C_4$ alkyl group with or without substituent(s);

R₁ and R₂ independently represent hydrogen, or linear or branched alkyl, cycloalkyl, alkoxyalkyl or cycloalkoxyalkyl having 1 to 10 carbon atoms with or without substituent(s);

m represents a number of 1 to 8; and the molar ratio $x:y:z$ is $(0.005–0.9):(0.001–0.9):(0.001–0.9)$.

9. The process of claim 8, wherein the amount of said photoresist polymer present in said composition is between 10 and 30% by weight based on the amount of said solvent.

10. The process of claim 8, wherein said solvent is selected from the group consisting of cyclohexanone, methyl 3-methoxypropionate, ethyl 3-ethoxypropionate, ethyl lactate, propylene glycol methyl ether acetate, and mixtures thereof.

11. The process of claim 8, wherein said photoacid generator is an onium salt or an organic sulfonic acid.

12. The process of claim 8, wherein the amount of said photoacid generator present in said composition is between 0.01 and 10% by weight based on the amount of said photoresist polymer.

* * * * *